United States Patent [19]
Thal et al.

[11] Patent Number: 5,480,884
[45] Date of Patent: Jan. 2, 1996

[54] COMPOUNDS HAVING A GUANIDINE STRUCTURE

[75] Inventors: Claude Thal, Sceaux; Catherine Quirosa-Guillou, Verrieres Le Buisson; Pierre Potier, Paris; Dolor Renko, Gif Sur Yvette; Jean-Pierre Zanetta, Griesheim/Souffel; Marie-Madeleine Portier, Verrieres Le Buisson; Monique Sensenbrenner, Strasbourg; Janine Koenig; Herbert Koenig, both of Bordeaux, all of France

[73] Assignee: Centre National De La Recherche Scientifique, Paris, France

[21] Appl. No.: 90,188

[22] PCT Filed: Nov. 20, 1992

[86] PCT No.: PCT/FR92/01080

§ 371 Date: Jul. 22, 1993

§ 102(e) Date: Jul. 22, 1993

[87] PCT Pub. No.: WO93/10102

PCT Pub. Date: May 27, 1993

[30] Foreign Application Priority Data

Nov. 22, 1991 [FR] France .................... 91 14474

[51] Int. Cl.⁶ .................... A61K 31/505; A61K 31/415; C07D 239/42; C07D 233/88
[52] U.S. Cl. .................... 514/275; 514/386; 514/399; 544/322; 544/332; 548/318.1; 548/318.5; 548/331.5; 548/341.5
[58] Field of Search .................... 514/275, 386, 514/399, 634, 534, 538; 544/322, 332; 548/318.1, 318.5, 331.5, 333.1, 335.1, 341.5; 560/115, 157, 159; 564/237, 240

[56] References Cited

U.S. PATENT DOCUMENTS

2,145,011  1/1939  Albertlandolt et al. ............... 564/240

FOREIGN PATENT DOCUMENTS

3312516  10/1984  Germany .................... 564/237
2231047  11/1990  United Kingdom ........... 564/240
8800181  1/1988  WIPO .................... 564/237

OTHER PUBLICATIONS

Christopher et al. J. Am. Chem. Soc. 90(1), 113–120, 1968.
Vincent et al. J. Org. Chem. 28, 123–129, 1963.
E. Boschetti et al., "Synthesis and Pharmacologic Classification of New Hypotensive Agents", Chemical Abstracts, vol. 70, 1969.
C. M. Gupta, "Novel Glass of Hypoglecemic Agents", Chemical Abstracts, vol. 75, p. 450, col. 1, 1971.
Y.-K. Kim et al., "Synthesis and Curing Study of 5-5 Ring Fused Polyimide Based on Imidazole", Macromolecules, vol. 24, No. 23, pp. 6357–6360, 1991.

*Primary Examiner*—Yogendra N. Gupta
*Attorney, Agent, or Firm*—Foley & Lardner

[57] ABSTRACT

Compounds are provided useful for promoting growth, repair and regeneration of a neuronal axon and for treating neuropathies and myopathies having formula I

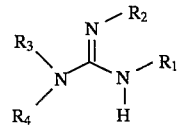

wherein $R_2$, $R_3$ and $R_4$ together with the nitrogen atoms to which they are attached forms a heterocyclic ring.

9 Claims, No Drawings

COMPOUNDS HAVING A GUANIDINE STRUCTURE

The present invention relates to new compounds of guanidine structure which promote the growth, repair and regeneration of the neuronal axon and capable of improving the condition of patients suffering from neuropathies and myopathies. More generally, these compounds may be useful in the domain of degenerative diseases of the nervous system.

Its subject is also preparation processes which make it possible to obtain the said compounds and the pharmaceutical compositions containing these compounds.

To the knowledge of the Applicant, no compounds are available in human therapy which act on the regeneration of the peripheral nerve and which are capable of having a beneficial effect on neuromuscular disorders.

A compound, isaxonine or 2-(isopropylamine)pyrimidine, having very advantageous pharmacological properties, has indeed already been described in "La Nouvelle Presse Médicale", Masson, 1982, 16 (11), 1193–1280: however, marketed under the name of Nerfactor, it had to be withdrawn from the market on the grounds of hepatotoxicity.

Moreover, in the journal "Thérapie" (1968, XXIII, pp. 1221–1232), veratrylguanidine and the hemisulfate of this compound have been described as antihypertensives.

However, the properties of these compounds in neurotherapy have, to the knowledge of the Applicant, never been described.

The subject of the invention is therefore to provide new compounds (leaving aside veratrylguanidine and its hemisulfate salt), useful in the domain of neuronal regeneration, which are therefore intended to have beneficial effects in diseases relating thereto such as myopathy.

According to the invention, the compounds correspond to the formula:

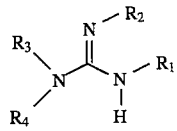

in which:
$R_1$ is an isopropyl radical, a benzyl radical which is optionally substituted by one or more $(C_1-C_4)$alkoxy radicals or a radical:

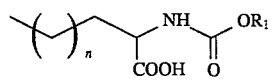

$R_2$, $R_3$ and $R_4$ together with the nitrogen atoms to which they are attached and the carbon atom to which the said nitrogen atoms are attached form a pyrimidine ring of formula II or a pyrimidinium ring of formula IIa:

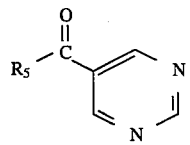

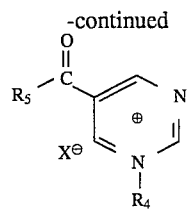

in which:
n= 0, 1, 2,
$R_4$ is a $(C_1-C_4)$alkyl radical, a $(C_7-C_9)$aralkyl radical, a phenyl radical or a hydrogen atom,
$R_8$ is a $(C_1-C_4)$alkyl radical, a $(C_7-C_9)$aralkyl radical and in general $COOR_8$ may be an amine-protecting group,
$R_8$ is a hydroxyl radical, a $(C_1-C_4)$alkoxy radical or an amino radical
$X^-$ is a pharmacologically acceptable cation
or $R_2$, $R_3$ and $R_4$ together form with the nitrogen atoms to which they are attached and the carbon atom to which the said nitrogen atoms are attached an imidazole ring of formula:

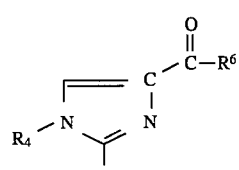

or 1,6-dihydropyrimidine of formula:

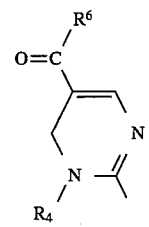

$R_6$ having one of the meanings of $R_5$,
or $R_2$, $R_3$ together form with the nitrogen atoms to which they are attached and the carbon atom to which the said nitrogen atoms are attached a ring of formula:

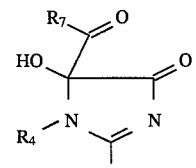

$R_7$ being a $(C_1-C_4)$alkoxy radical or a 1-glyceryl radical with in this latter case $R_1$ which may correspond to a hydrogen atom,
and the pharmacologically acceptable salts of these compounds, with the exception of veratrylguanidine and the hemisulfate thereof.

The invention also relates to the pharmacologically acceptable salts of these compounds, especially the lactate, fumarate, hydrochloride, maleate, malate, ketoglutarate, glutarate, phenoxyacetate, sulfonate, picrate, tartrate and methanesulfonate.

According to a preferred variant of the invention, $R_1$ is an isopropyl radical or a di- or trimethoxybenzyl radical or the radical:

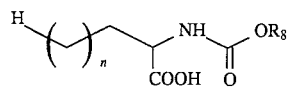

According to a second preferred variant of the invention, taken or otherwise in combination with the one above, $R_4$ is a methyl, ethyl, n-propyl or benzyl radical.

According to a third preferred variant, the invention relates to the lactate, fumarate, hydrochloride, maleate, malate, ketoglutarate, glutarate, phenoxyacetate, sulfonate, picrate, tartrate, methanesulfonate of veratrylguanidine.

The invention also relates to the medicinal products consisting of one of the compounds according to the invention, as has just been described above, and the pharmaceutical compositions containing at least one of these medicinal products and an acceptable carrier. These medicinal products and compositions are useful in the medical treatment in man or animals of certain disorders linked to the functioning of the nervous system.

The medicinal products and compositions may thus be advantageously intended to play a part in an effective therapy against degenerative diseases of the peripheral nervous system and against neuromuscular disorders such as myopathy.

The pharmaceutical compositions are especially formulated so as to be ingested orally or so as to be injected. However, other modes of administration may also be envisaged within the framework of the present invention.

The dosage will depend in part on the disease to be treated as well as on its severity and also on the type of individual (weight, age).

For the compounds already known, such as veratrylguanidine or the hemisulfate thereof, the subject of the invention is the use of these compounds for the manufacture of a medicinal product useful in treating neuromuscular diseases.

The invention also relates to the processes for preparing the compounds according to the invention.

One process for preparing the compounds of formula (I) in which $R_2$, $R_3$ and $R_4$ together with the nitrogen atoms to which they are attached and the carbon atom to which the said nitrogen atoms are attached form a pyrimidine ring of formula II, consists in placing an acid salt of guanidine (for example the hydrogen sulfate) of formula:

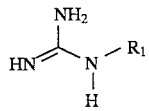

I into contact with a $(C_1-C_4)$alkoxymalonaldehyde of formula:

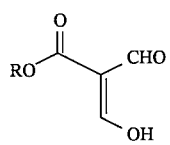

VI in the presence of an acid acceptor (such as a tertiary [sic] amine such as pyrrolidine) and optionally a protic polar solvent such as methanol.

The compounds obtained in a non-salified form are then converted to an acid by hydrolysis in a known manner, and optionally converted to a carboxamide also in a known manner (for example by reaction with aminochloromethylaluminum).

Moreover, the alkylation of these pyrimidines of formula II in whichever form (acid, ester or amide) may be carried out by the action of a dialkyl sulfate in aprotic polar solvent to give the acid sulfate purified in the form of the corresponding 1-alkylpyrimidinium hydroxide which may then be converted to another salt (for example the methanesulfonic acid salt).

The hydroxide formed may also be converted to 1,6-dihydro-1-alkylpyridimine [sic] of formula IV by reaction with a reducing agent, especially with sodium tetraborohydride optionally in the presence of a protic polar solvent (especially ethanol).

A process for preparing the compounds of formula (I) in which $R_2$, $R_3$ and $R_4$ together form with the nitrogen atoms to which they are attached and the carbon atom to which the said nitrogen atoms are attached an imidazole ring of formula III consists in partially decarboxylating the 4,5-dicarboxyimidazoles by heating optionally in the presence of a polar solvent such as N,N-dimethylacetamide.

The 4,5-dicarboxyimidazoles are obtained by saponification of the corresponding 4,5-dicyano compounds in a known manner. The latter are either commercial products or obtained in a known manner.

One preparation process for example consists in alkylating in the 1-position the 2-bromo-4,5-dicyanoimidazoles by reaction with a dialkyl sulfonate. This latter compound is substituted in the 2-position by an amine $H_2N$—$R_1$ and then treated with a strong base (for example NaOH) and acidified (for example concentrated HCl).

The starting 2-bromo-4,5-dicyanoimidazole compounds are obtained in a known manner by bromination of the 4,5-dicyanoimidazoles.

Another process for preparing imidazoles according to the invention in which $R_4$ is a hydrogen atom (therefore with the existence of a tautomerism) consists in carrying out the sequence of reactions according to the following scheme:

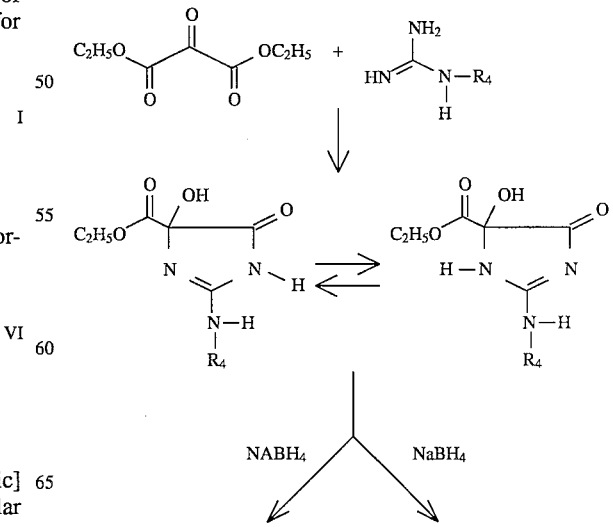

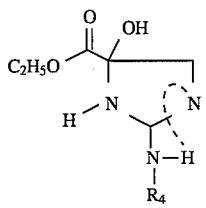

-continued

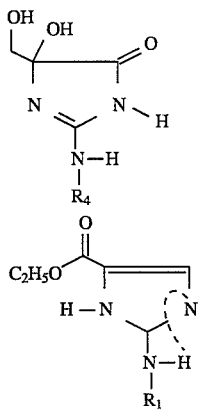

One process for preparing the guanidines of formula (I) or their pharmacologically acceptable salts consists in starting with the corresponding S-alkylthiourea which is reacted with an alkylamine $R_1NH_2$ in a known manner.

One process for the manufacture of the compounds of formula (I) in which $R_2$ and $R_3$ together form with the nitrogen atoms to which they are attached and the carbon atom to which the said nitrogen atoms are attached a ring of formula V, where $R_7$ is a ($C_1$–$C_4$)alkoxy radical, consists in reacting the corresponding guanidine of formula I with a dialkylketomalonate optionally in a protic polar medium according to the reaction scheme above.

In the case where $R_7$ is a 1-glyceryl radical, a preparation process consists in condensing a guanidine of formula (I) with the oxidized form of ascorbic acid, it being possible for the amine to be optionally dealkylated according to the following reaction scheme:

The examples below illustrate the invention:

EXAMPLE 1

1-Methyl-2-isopropylamino-5-methoxycarbonyl-1,6-dihydropyrimidine

To 10.5 g (32 mmol) of 1-methyl-2-isopropylamino-5-methoxycarbonylpyrimidinium hydroxide in 180 ml of anhydrous ethanol, are added by portion under argon at −40° C. sodium borohydride (2.8 g; 73 mmol). The mixture is stirred under argon for one hour at room temperature. After evaporation of the ethanol, the reaction medium is extracted with dichloromethane and water. The organic phases are washed with a saturated sodium chloride solution and then dried over sodium sulfate. Purification on silica gel (200 mb; eluent: 10% MeOH/$CH_2Cl_2$) of the oil obtained by evaporation of the organic phases gives 7 g (yield: 100%) of corresponding dihydro ester.

Melting point: 83° C.

The 1-methyl-2-isopropylamino-6-methoxycarbonylpyrimidinium hydroxide is obtained in the following manner:

A mixture of 27.45 g (0.140 mol) of 2-isopropylamino-5-methoxycarbonylpyrimidine and 56 ml (2 eq; 0.59 mol) of dimethyl sulfate in 440 ml of anhydrous tetrahydrofuran is refluxed for 24 hours. The reaction medium is extracted with ethyl acetate and water. Purification on silica gel (eluent: 95 $CH_2Cl_2$[sic]/5% MeOH/saturation with gaseous $NH_3$) of the oil resulting from the evaporation of the aqueous phases gives 37.2 g of 1-methyl-2-isopropylamino-5-methoxycarbonylpyrimidinium hydroxide (yield: 82%).

EXAMPLE 2

2-Isopropylamino-5-methoxycarbonylpyrimidine

A mixture of 11.62 g (77.5 mmol) of isopropylguanidine hydrogen sulfate, 32 ml (5 eq; 0.37 mol) of freshly distilled pyrrolidine in 230 ml of anhydrous methanol is refluxed for twenty minutes. A methanolic solution (60 ml) of methoxymalonaldehyde (1 eq; 77.5 mmol; 10 g) is added to the above solution at 0° C. as well as 140 g of molecular sieve (4 A °). The reaction medium is stirred under argon and under reflux for 24 hours. The molecular sieves are removed by filtration and then rinsed with methanol. Evaporation of the filtrate gives a residue which is taken up with ethyl acetate and then acidified with a 1N hydrochloric acid solution. The organic phases are washed with a saturated sodium chloride solution, dried over sodium sulfate, evaporated and purified on silica gel under 200 mb (eluent: 50 ethyl acetate/50 heptane).

Weight: 11.27 g (yield: 75%).

Melting point 102° C.

EXAMPLE 3

1-Methyl-2-isopropylamino-5-methoxycarbonyl-pyrimidinium sulfate 1.09 mlg [sic] (16.78 mol; 1.61 g) of methanesulfonic acid is added to a solution of 1-methyl-2-isopropylamino-5-methoxycarbonylpyrimidinium hydroxide (3.48 g; 15.35 mol) dissolved in 100 ml of anhydrous tetrahydrofuran. The mixture is stirred under argon at room temperature for one hour. The precipitate which forms is filtered and then rinsed with ether.

Weight: 3.74 g (yield: 80%).

Melting point: 209° C.

EXAMPLE 4

2-Isopropylamino-5-carbamoylpyrimidine 30.6 ml (61.2 mmol) of a 2N solution of trimethylaluminum in toluene are slowly introduced into a suspension of ammonium chloride (61.2 mmol; 3.26 g) in 71 ml of anhydrous benzene at 0° C. The addition completed, the mixture is stirred under argon for one to two hours until the evolution of methane is exhausted.

To 92 ml of the above solution (6 eq of reagent), a solution of 2-isopropylamino-5-methoxycarbonylpyrimidine (0.102 mol; 2 g) in 40 ml of anhydrous benzene is added with a cane. After stirring for 48 hours at room temperature under argon, the mixture is neutralized with 5% hydrochloric acid and then extracted with dichloromethane. The organic phases are removed and the aqueous phases are filtered and evaporated. The amide in powder form is obtained with a yield of 80% after purification on silica gel (eluent: 80% $CH_2Cl_2$/20% MeOH/0.7% $NH_3$ in aqueous solution at 33%).

EXAMPLE 5

2-Isopropylamino-5-carboxypyrimidine 6 ml of a 1N solution of sodium hydroxide are added to a solution of 2-isopropylamino-5-methoxycarbonylpyrimidine (1 g; 5.12 mmol) in 33 ml of methanol. The mixture is refluxed (66° C.) for two hours. A minimum of water is added in order to dissolve the precipitate which forms; the methanol is evaporated under reduced pressure. The remaining solution is acidified at 0° C. with 2N hydrochloric acid. The precipitate obtained is filtered, washed with water and then dried to give 850 mg (92%) of acid.

EXAMPLE 6

1 - Methyl -2-isopropylamino-5-carbamoyl-1,6-dihydropyrimidine 49.7 ml (99.5 mmol ) of a 2N solution of trimethylaluminum in toluene are slowly introduced into a suspension of ammonium chloride (99.5 mmol; 5.32 g) in 105 ml of anhydrous toluene at 0° C. The addition completed, the mixture is stirred under argon for one to two hours until methane evolution is exhausted.

A solution of 1-methyl-2-isopropylamino-5-methoxycarbonyl- 1,6-dihydropyrimidine (3.4 g; 0.16 mol) in 175 ml of anhydrous toluene is added with a cane to 144 ml of the 0.67M solution of aminochloromethylaluminum (6 eq of reagent). After stirring for 60 hours at room temperature under argon, the mixture is slowly neutralized at 0° C. with 1N hydrochloric acid (350 ml) and then extracted with ethyl acetate. The aqueous phases are evaporated, taken up with ethanol saturated with ammonia and silica (which retains the aluminum salts); this mixture is filtered and then evaporated. After several flash chromatographies on silica gel (200 mb; 5–30% MeOH/$CH_2Cl_2$/$NH_3$ saturation) of the filtrate, 2.28 g of amide are obtained with a yield of 72%.

Melting point: 179°–180° C.

EXAMPLE 7

α-N-Boc-δ-N-((2-pyrimidinyl-5-methoxycarbonyl)-L-ornithine

The mixture of 4 g (14.5 mmol) of alpha-N-Boc-L-arginine (commercial), 2.84 g (1.5 eq; 21.8 mol) of methoxymalonaldehyde, 3.65 ml of freshly distilled pyrrolidine, 10 g of activated molecular sieve 4A°, in 30 ml of anhydrous methanol is heated at 50° C. for 24 hours under argon. After removal of the molecular sieves by filtration and evaporation of methanol, the reaction medium is extracted with water and dichloromethane. The aqueous phases are evaporated and then purified on silica gel (200 mbar; eluent: 80% $CH_2Cl_2$/20% MeOH/$NH_3$ in aqueous solution at 33%, 0.7 ml per 100 ml). 4.21 g are obtained (yield: 80%).

EXAMPLE 8

δ-N-(2-Pyrimidinyl-5-methoxycarbonyl)-L-ornithine 0.77 ml (4 eq; 5.43 mmol) of iodotrimethylsilane is added to 500 mg (1.35 mmol) of pyrimidine of Example 7 dissolved in 20 ml of chloroform. After stirring for one hour at room temperature under anhydrous atmosphere, water is added as well as dichloromethane. Evaporation of the aqueous phases gives a residue which is purified on silica gel.

EXAMPLE 9

2-Veratrylamino-5-carboxypyrimidine 0.4 ml of a 1N solution of sodium hydroxide is added to a methanolic solution (1 ml) of 2-veratrylamino- 5-carboxymethylpyrimidine (100 ml; 3.3 mmol). The mixture is refluxed for two hours. The methanol is evaporated under reduced pressure. The remaining solution is acidified with 2N hydrochloric acid; the precipitate which forms is filtered, washed with water and then dried (yield: 90%).

EXAMPLE 10

2-Veratrylamino-5-methoxycarbonylpyrimidine

A mixture of 21.92 g (0.1 mmol) of veratrylguanidine obtained according to "Thérapie" (op.cit.), 41.7 ml (0.5 mol) of freshly distilled pyrrolidine, 15 g of methoxymalonaldehyde, 180 g of molecular sieve (4 A° ) in 300 ml of anhydrous methanol is refluxed under argon for twenty-four hours. The molecular sieves are removed by filtration and then rinsed with methanol and chloroform. Evaporation of the filtrate gives a residue which is taken up with ethyl acetate and then acidified with a 1N solution of hydrochloric acid. The organic phases are washed with a saturated sodium chloride solution, dried over sodium sulfate, evaporated and purified on silica gel (eluent: 50 ethyl acetate/50 heptane) (yield: 40%).

EXAMPLE 11

1-Methyl-2-veratrylamino-5-methoxycarbonyl-1,6-dihydropyrimidine 0.170 g (3 eq) of sodium borohydride is added to 0.400 g of 1-methyl-2-veratrylamino-5-methoxycarbonylpyrimidinium hydroxide dissolved in 50 ml of ethanol. The mixture is stirred under argon at room temperature for three hours. After evaporation of the ethanol, the medium is extracted with dichloromethane and water. The organic phases are washed with a saturated sodium chloride solution and then dried over sodium sulfate. The oil resulting from evaporation of the organic phases, purified on silica gel under medium pressure (eluent: 15% MeOH/$CH_2Cl_2$) gives 467 mg (yield: 98%) of the corresponding 1,6-dihydropyrimidine.

EXAMPLE 12

1-Methyl-2-veratrylamino-5-methoxycarbonyl-pyrimidinium hydroxide

A mixture of 2.62 g .(8.6 mmol) of 2-veratrylamino-5-methoxycarbonylpyrimidine and 3.28 ml (4 eq) of dimethyl sulfate in 60 ml of anhydrous THF is refluxed for forty-eight hours. The mixture is extracted with ethyl acetate and water. Purification on silica gel (eluent: 3% MeOH/ $CH_2Cl_2$/$NH_3$ in aqueous solution at 33%, 5.5 ml/100) of the oil resulting from evaporation of the aqueous phases gives 2.2 g of salt (yield: 76%).

EXAMPLE 13

1-Methyl-2-veratrylamino-5-methoxycarbonyl-pyrimidinium sulfate

To 400 mg of 1-methyl-2-veratrylamino-5-methoxycarbonylpyrimidinium hydroxide dissolved in 15 ml of anhydrous tetrahydrofuran, are added 85 µl (1.1 eq; 1.31 mmol) of methanesulfonic acid. The mixture is stirred under argon at room temperature for one hour. The precipitate is filtered, rinsed with tetrahydrofuran and ether and then dried (weight: 490 mg—yield: 96%).

EXAMPLE 14

Veratrylguanidine methanesulfonate

Methanesulfonic acid (7.8 ml; 0.120 mol) is introduced into a suspension of veratrylguanidine (25 g; 0.119 mol) in 240 ml of methanol. The mixture is stirred at room temperature for one hour. The methanol is evaporated under vacuum, the oil obtained is precipitated by stirring for 15 min in tetrahydrofuran. The white solid is filtered, rinsed with tetrahydrofuran and ether and then dried under vacuum. 30 g of veratrylguanidine methanesulfonate are obtained with a yield of 82%.

EXAMPLE 15

1-Methyl-2-isopropylamino-4-carboxyimidazole

A mixture of 1-methyl-2-isopropylamino-4,5-dicarboxyimidazole (910 mg; 4 mmol) and 20 ml of N,N-dimethylacetamide is heated at 180° C. under argon for three hours. The solvent is evaporated under reduced pressure; the residue, taken up with minimum ethanol, is precipitated with tetrahydrofuran. The mother liquors are concentrated until precipitation is obtained. The 1-methyl-2-isopropylamino-4-carboxyimidazole is obtained with a yield of 88%.

(m= 650 mg).

Melting point: 247° C.

EXAMPLE 16

1-Methyl-2-isopropyl-4-methoxycarbonylimidazole 400 mg of 1-methyl-2-isopropylamino-4-carboxyimidazole are solubilized in 25 ml of anhydrous methanol. The solution is cooled to 0° C. saturated with hydrochloric acid and then refluxed for twelve hours. After cooling, the excess acid is expelled with an argon stream. The medium is neutralized by addition of sodium carbonate and evaporated. The residue, taken up with water, is extracted with dichloromethane. The organic phases, dried over sodium sulfate and evaporated, give a residue which is washed with ether and then dried under vacuum.

m= 384 mg; yield: 89%.

Melting point: 198° C.

EXAMPLE 17

2-Isopropylamino-4-oxo-5-ethoxycarbonyl-5-hydroxy-$\Delta_2$-imidazoline 5.72 g (0.0191 mol) of isopropylguanidine hydrogen sulfate are desalified with a methanolic solution (20 ml) of sodium hydroxide (0.038 mol; 1.53 g) at room temperature under argon for one hour. The resulting precipitate is filtered; the filtrate is evaporated. The isopropylguanidine is taken up in ethanol and again filtered. The ethanolic filtrate is concentrated.

3.85 g (0.0382 mol) of isopropylguanidine and 10 g of diethylacetomalonate in 150 ml of ethanol are heated for 10 hours at 50° C. Evaporation of the ethanol gives a residue which is purified by flash chromatography on silica gel 60 (eluent: 15 MeOH/$CH_2Cl_2$) (m= 7 g; yield: 80%). The compound exists in two forms A and B in equilibrium.

EXAMPLE 18

2-Amino-4-(1',2',3'-trihydroxybutanoyl)-4-hydroxy-5-oxoimidazoline

A mixture of L-ascorbic acid (0.314 mol; 55.4 g) and p-benzoquinone in 470 ml of ethanol is stirred in darkness under argon for 90 min; then an ethanolic solution (100 ml) of guanidine (0.157 mol) (previously desalified with sodium hydroxide in ethanol) is then added. The medium is stirred at room temperature under argon in darkness for 6 h. The precipitate which forms is filtered, washed with ethanol and dried under vacuum (m= 30 g; yield= 100%).

EXAMPLE 19

2-Amino-4- (1',2',3'-trihydroxybutanoyl) -5-oxoimidazole

A solution of 2 g of the crude compound of Example 18 (8.23 mmol), solubilized in 80 ml of anhydrous ethanol, is refluxed for one hour. After evaporation and purification on silica gel (eluent: 35% MeOH/5% $H_2O$/$CH_2Cl_2$ then 40% MeOH/5% $H_2O$/$CH_2Cl_2$) 400 mg are obtained with a yield of 22%.

Isopropylguanidine (Example 20), isaxonine (Example 21) and isopropylguanidine chloride (Example 22) were also obtained according to a known technique.

Biological Trials

A—Effect on the neuritic development of the spinal ganglia

Experimental procedure:

Ganglia collected from newborn rats are cultured in 96-well flat-bottomed plates in a DMEM medium (Gibco) to which are added 5% fetal calf serum (FCS) and 10 mM of Ara-C (cytosine-β-D-arabinofuranoside).

After one day, the various compounds to be tested and control solutions are added.

Two days later, the culture is stopped and explants are photographed at low magnification under a phase contrast microscope or using a conventional microscope after staining with toluidine blue after fixing with mixtures of aldehydes. Taken into account in the evaluations are the average diameter of the extension of the neuritic bundles, their ramifications, their association with glial cells and dead cells.

Compounds tested:

Compounds 1 to 8, 14, 18 and 21 were tested at three different concentrations: $10^{-5}$, $10^{-6}$ and $10^{-7}$M in the presence or in the absence of 50 IU/ml of NGF (Anglo Saxon acronym designating nerve growth factor). The aim of the experiments in the presence of NGF was on the one hand a comparison with the products tested and on the other hand the observation of a possible modification of the NGF effect (cell death, induction of neuritic ramifications).

Without additive other than PBS, which is used to solubilize the various compounds, the presence of rare short extensions and of a fairly large number of dead cells is observed. In the presence of the control NGF, numerous fine and long, not highly branched, extensions are observed.

The effect of the various products is evaluated by comparison with the reference control: product alone relative to PBS on the one hand, product+ NGF relative to NGF on the other hand. Moreover, the positive effect of a product used alone is compared with that of NGF.

The compound of Example 3 in the presence of NGF causes a substantial modification of the neurites; the latter are longer and especially exhibit a substantial arborization with numerous cells attached to the extensions. The compound of Example 14 in the presence of NGF causes lengthening of the neurites (approximately double that for cultures in the presence of NGF alone). There is also an effect which promotes cross-linking of the neurites (fewer neurites of larger diameter).

Compounds 3 and 14, used alone, accentuate the neuritic development relative to the control PBS. The morphological appearance of the extensions is identical to those for NGF and the effectiveness appears similar to that for this growth factor.

The compound of Example 5, used alone at low concentration or in the presence of NGF ($10^{-7}$M), exhibits a positive effect with increase in the number of extensions.

The compounds of Examples 7 and 22 exhibit a positive effect revealed alone or in synergy with NGF and characterized by an increase in the length of the neurites.

With Examples 2, 6 and 21, the presence of a larger number of extensions is observed without increase in their length.

B—Effect on chicken and rat neurones and glial cells in primary culture

The compounds of Examples 14 and 21 were tested on the survival and growth of the neurites of neurones of the central and peripheral nervous systems in primary culture, as well as on the proliferation and morphological modification of the astrocytes.

Experimental procedure:

1. 14-day old rat embryo brain neurones

The neurones are dissociated from the cerebral hemispheres and are cultured on polylysine in Petri dishes in the presence of nutrient medium lacking chemically defined serum.

2. Neurones of spinal and ciliary ganglia of 8-day old chicken embryo

The dissociated neurones are cultured on polyornithine in a nutrient medium containing 20% fetal calf serum.

3. Newborn rat brain astrocytes

The dissociated cells are cultured directly on the surface of the plastic of the Petri dish in defined medium.

Compounds 14 and 21 were added at concentrations of $10^{-4}$ to $10^{-8}$M immediately after inoculation and at each change of medium.

On the neurones isolated in pure culture, compound 21 stimulates the neuritic growth of the neurones of the central nervous system and compound 14 promotes the survival and neuritic growth of the neurones of the spinal ganglia (peripheral nervous system). Furthermore, compound 14 has no toxic effect on the supporting cells (astrocytes). These compounds, which are capable of regulating neuronal survival and neuritic growth, constitute a therapeutic route in neuropathies and myopathies.

C—Neurotrophic effect in the neuromuscular axis

Compounds 1, 3 and 14 were tested in vivo on the regeneration of the axons and their remyelination in Trembler mice, an animal model of Charcot-Marie-Tooth's neuropathy in man.

Compounds 1, administered by subcutaneous injection (100 mg/kg), and 14 administered by intraperitoneal injection (50 mg/kg), promote intraneural axonal "sprouting" (+25% and +20%) and they accelerate demyelination which characterizes the Trembler mutation (−25%).

Compound 3 also promotes demyelination. After 40 days of daily injections, only 22% of the nerve fibers are myelinated instead of 32% in the controls.

Compounds 1, 3, 7 and 14 were also tested in vitro at $10^{-3}$M, $10^{-5}$M and $10^{-7}$M in the following cultures:

1) 14-day old rat embryo spinal cord cells;

2) myoblasts of normal mice and Mdx mice, an animal model similar to Duchenne's myopathy in man 3) co-cultures of myoblasts (19-day old rat embryos) and neurons (14-day old rat embryos) and 4) 3T3 cells, fibroblast line.

Compounds 1, 3 and 14 promote the formation of cell clusters. The emergence and development of neurites. Compound 14 is the most active of the three.

In the neuron-muscle co-cultures, compounds 3 and 14 promote neuritic development and their ramification.

In the co-cultures, the neuromuscular junctions (synapses) are detected by co-localization of acetylcholinesterase and the acetylcholine receptors.

Compound 7 increases the number of synapses by 60% at $10^{-3}$M.

The increase in the number of synapses formed under the influence of compound 7 is dose-dependent.

We claim:

1. A compound of formula:

$$\underset{R_4}{\overset{R_3}{\diagdown}}N\diagdown\underset{\diagup}{\overset{N-R_2}{\overset{\|}{C}}}N\diagup\overset{R_1}{\underset{H}{\diagdown}}\quad I$$

wherein $R_1$ is an isopropyl radical, a benzyl radical which is optionally substituted by one or more $(C_1-C_6)$ alkoxy radicals or a radical:

$$-(CH_2)_n-CH(COOH)-NH-C(=O)-OR_8$$

$R_2$, $R_3$ and $R_4$ together with the nitrogen atoms to which they are attached and the carbon atom to which the said nitrogen atoms are attached form a pyrimidine ring of formula II or a pyrimidinium ring of formula IIA:

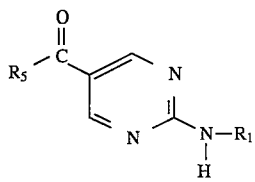  II

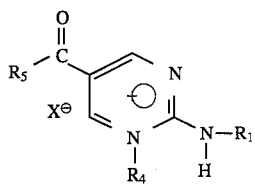  IIA in which:
n= 0, 1, 2,
$R_4$ is a ($C_1$–$C_4$) alkyl radical, a ($C_7$–$C_9$) aralkyl radical, a phenyl radical or a hydrogen atom,
$R_8$ is a ($C_1$–$C_4$) alkyl radical or a ($C_7$–$C_9$) aralkyl radical,
$R_5$ is a hydroxyl radical, a ($C_1$–$C_4$) alkoxy radical or an amino radical,
X is a pharmacologically acceptable cation or $R_2$, $R_3$ and $R_4$ together form with the nitrogen atoms to which they are attached and the carbon atom to which the said nitrogen atoms are attached an imidazole ring of the formula:

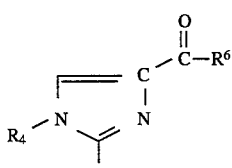  III or 1,6-dihydropyrimidine of formula

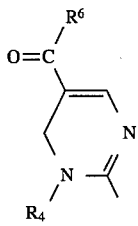  IV $R_6$ having one of the meanings of $R_5$ or $R_2$, $R_3$ together form with the nitrogen atoms to which they are attached and the carbon atom to which the said nitrogen atoms are attached a ring of formula:

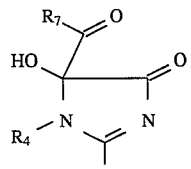  V $R_7$ being a ($C_1$–$C_4$) alkoxy radical or a glyceryl radical, or a pharmacologically acceptable salt thereof.

2. Compounds according to claim 1, characterizied in that $R_1$ is an isopropyl radical or a di- or trimethoxy benzyl radical or the radical:

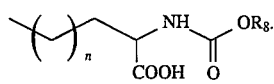

3. A compound according to claim 1, characterized in that $R_4$ is a methyl, ethyl, n-propyl or benzyl radical.

4. A compound according to claim 1, characterized in that they are chosen from lactate, fumarate, hydrochloride, maleate, malate, ketoglutarate, glutarate, phenoxyacetate, sulfonate, picrate, tartrate, methanesulfonate and veratrylguanidine.

5. Pharmaceutical composition containing at least one compound according to claim 1 and a pharmacologically acceptable inert carrier.

6. A method of using the compound of claim 1 in order to promote the growth, repair, and regeneration of a neuronal axon comprising administering to a patient in need thereof a therapeutically effective amount of the compound of claim 1.

7. A method of using the compound of claim 1 in the treatment of neuropathies comprising administering to a patient in need thereof a therapeutically effective amount of the compound of claim 1.

8. A method of using the compound of claim 1 in the treatment of myopathies comprising administering to a patient in need thereof a therapeutically effective amount of the compound of claim 1.

9. 1-Methyl-2-isopropylamino-4-carboxy-imidazole.

* * * * *